(12) United States Patent
Jenkins et al.

(10) Patent No.: US 8,852,596 B1
(45) Date of Patent: Oct. 7, 2014

(54) **DETECTION OF *GIARDIA LAMBLIA* TROPHOZOITES AND CYSTS AND PROTECTION AGAINST *G. LAMBLIA* INFECTION**

(71) Applicant: The United States of America, as represented by the Secretary of Agriculture, Washington, DC (US)

(72) Inventors: Mark C. Jenkins, Davidsonville, MD (US); Ronald Fayer, Ellicot City, MD (US); Monica Santin, Odenton, MD (US); Dumitru Macarisin, Hagerstown, MD (US); Celia O'Brien, Ellicott City, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/651,830

(22) Filed: Oct. 15, 2012

(51) Int. Cl.
*A61K 39/395* (2006.01)

(52) U.S. Cl.
USPC .................................. 424/151.1; 424/141.1

(58) Field of Classification Search
None
See application file for complete search history.

(56) References Cited

U.S. PATENT DOCUMENTS 6,908,739 B2 * 6/2005 Buechler et al. ............... 435/7.1

OTHER PUBLICATIONS rossley, R. et al., Assembly of 2.5 nm Filaments from Giardin, A Protein Associated with Cytoskeletal Microtubules in *Giardia*, J. Cell Sci., 1985, 205-231, vol. 78.
Elmendorf, H.G. et al., The Cytoskeleton of *Giardia lamblia*, International Journal for Parasitology, 2003, 3-28, vol. 33.
Heyworth, M.F. et al., *Giardia muris*: Evidence for a B-Giardin Homologue, 1999, 284-287, vol. 91.
Holberton, D. et al., Segmented a-Helical Coiled-coil Structure of the Protein Giardin from the *Giardia* Cytoskeleton, J. Mol. Biol., 1988, 789-795, vol. 204.
Holberton, D.V. et al., Isolation of the Cytoskeleton from *Giardia*. Tubulin and a Low-Molecular-Weight Protein Associated with Microribbon Structures, J. Cell Sci., 1981, 139-166, vol. 47.
Jenkins, M.C. et al., Antibodies to the Ventral Disc Protein—Giardin Prevent in Vitro Binding of *Giardia lamblia* Trophozoites, J. Parasitol., 2009, 895-899, vol. 95(4).
Nohria, A. et al., Identification and Characterization of y-giardin and the y-giardin gene from *Giardia lamblia*, Molecular and Biochemical Parasitolygy, 1992, 27-38, vol. 56.
Palm, D. et al., Developmental Changes in the Adhesive Disk During *Giardia* Differentiation, Molecular and Bichemical Parasitology, 2005, 199-207, vol. 141.

* cited by examiner

*Primary Examiner* — Gary B. Nickol
*Assistant Examiner* — Khatol Shahnan-Shah
(74) *Attorney, Agent, or Firm* — John D. Fado; Evelyn M. Rabin; Gail E. Poulos

(57) ABSTRACT

Immunolocalization of β- and δ-giardin in *Giardia lamblia* trophozoites revealed that both giardins are strictly associated with the ventral disc. Optical sectioning of immunolabeled ventral disc, together with quantitative co-localization of δ- and β-giardin immunoreactivity, demonstrated that δ-giardin is primarily localized to the ventral side, and β-giardin is localized to the dorsal side of the ventral disc. Antibodies to δ-giardin and β-giardin can both be used as diagnostic agents; anti-δ-giardin antibody can be used as a therapeutic reagent to inhibit binding of trophozoites to host cells.

8 Claims, 11 Drawing Sheets
(11 of 11 Drawing Sheet(s) Filed in Color)

DETECTION OF *GIARDIA LAMBLIA* TROPHOZOITES AND CYSTS AND PROTECTION AGAINST *G. LAMBLIA* INFECTION

BACKGROUND OF THE INVENTION

1. Field of the Invention

This invention relates to *Giardia lamblia*, a protozoan parasite that causes the diarrheal disease giardiasis in humans and other mammals. This invention relates to monoclonal and polyclonal antibodies which specifically bind to native and recombinant δ-giardin and β-giardin and the localization of the δ- and β-giardins within the ventral disc of *Giardia lamblia* trophozoites.

2. Description of the Relevant Art

*Giardia lamblia* (synonymous with *G. duodenalis* and *G. intestinalis*) is a bi-nucleate protozoan parasite that colonizes the upper part of the small intestine of humans and animals causing diarrheal disease. The study of *Giardia* biology and efforts to develop control strategies against the parasite have been greatly advanced by the complete sequencing of its genome (Morrison et al. 2007. *Science* 317:1921-1926). In order to maintain infection within the small intestine, trophozoites, the replicative stage of the parasite, must attach to the epithelial layer of the gut and to resist its peristaltic movement, bolus flow and continuous shedding of mucus and cells. Unlike other Diplomonadida, *Giardia* has a unique organelle, the ventral disc (Elmendorf et al. 2003. *International Journal for Parasitology*, 33:3-28), which is believed to play a key role in *Giardia* virulence by mediating attachment to host epithelial cells (Palm et al. 2005. *Mol. Biochem. Parasitol.* 141:199-207). The rigid structure of the ventral disc, also referred to as the adhesive or sucking disc, is supported by a spiral array of microtubules emanating from posterior flagellar bodies. Adjacent microtubules are connected to micro-ribbons and cross-bridges. In addition to highly conserved tubulin and actin components, the ventral disc is composed of proteins, identified as α-, β-, γ- and δ-giardins (Nohria et al. 1992. *Mol. Biochem. Parasitol.* 56:27-37). Of those, definite localization within the ventral disc has been shown only for β-giardin, also referred to as striated fibre assembline homolog (Crossley and Holberton. 1985. *J. Cell Sci.* 78:205-231; Elmendorf et al., supra; Holberton and Ward. 1981. *J. Cell Sci.* 47:139-166; Holberton et al. 1988. *J. Mol. Biol.* 204:789-795;). While giardins are components of the cytoskeleton, there are reports in *G. muris* that β-giardin may also be expressed on the trophozoite surface (Heyworth et al. 1999. *Exp. Paresitol.* 91:284-287) or associated with the ventral disc membrane in the bare zone (Palm et al., supra). Original conflicting evidence on the location of alpha giardins (the annexine homologs) has been resolved by the discovery of twenty-one different α-giardins that may be present on flagella, the ventral disc, or on the trophozoite surface (Weiland et al. 2005. *Internatl. J. Parasitol.* 35:617-626). It appears certain that α1- and α2-giardins are associated with the plasma membrane, and play some role in attachment of trophozoites to host cells (Aggarwal and Nash. 1989. *Infect. Immun.* 57:1305-1310; Wenmann et al. 1993. *Parasitol. Res.* 79:587-592; Weiland et al. 2003. *Internatl. J. Parasitol.* 33:1341-1351). Current knowledge of the γ- and δ-giardin localization in the ventral disc is limited. In recent studies it was shown that anti-recombinant δ-giardin antibodies preferably recognized the ventral disc and inhibited trophozoite binding to an inanimate surface (Jenkins et al. 2009. *J. Parasitol.* 95:895-899).

There is a need for diagnostic agents for specifically identifying *G. lamblia* trophozoites and for therapeutic agents useful for inhibiting or preventing attachment of *G. lamblia* trophozoites to host cells, to thereby inhibit, ameliorate, or prevent clinical giardiasis.

SUMMARY OF THE INVENTION

We have determined from co-localization analysis of δ-giardin and β-giardin on *G. lamblia* trophozoites that δ-giardin is present more ventrally than β-giardin on the ventral disc and that δ-giardin is therefore closest to the side of the ventral disc that makes contact with host cells.

In accordance with this discovery, it is an object of the invention to provide monoclonal or polyclonal antibodies that specifically bind to *G. lamblia* δ-giardin or to *G. lamblia* β-giardin.

It is another object of the invention to provide antibodies that specifically bind to *G. lamblia* δ-giardin.

It is an additional object of the invention to provide a composition containing anti-recombinant δ-giardin antibody or anti-recombinant β-giardin antibody for identifying the presence of native δ-giardin protein or native β-giardin protein of *G. lamblia*, respectively, thereby serving as a diagnostic for *G. lamblia*.

It is a further object of the invention to provide a method of diagnosing *G. lamblia* infection of a subject.

It is a still further object of the invention to provide a *G. lamblia* diagnostic kit, comprising an anti-recombinant δ-giardin-specific antibody and/or an anti-recombinant β-giardin-specific antibody and instructions for the use of the kit.

It is an additional object of the invention to provide a composition containing anti-recombinant δ-giardin antibody for inhibiting or preventing attachment of *G. lamblia* trophozoites to host cells, thereby inhibiting, ameliorating, or preventing clinical giardiasis.

It is another object of the invention to provide a method for inhibiting, ameliorating, or preventing clinical giardiasis in a mammal, particularly a human.

Also part of this invention is a kit, comprising an anti-recombinant δ-giardin antibody-containing composition for inhibiting, ameliorating, or preventing clinical giardiasis.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 3A shows antibodies to recombinant β-giardin followed by FITC (green)-labeled secondary antibodies; FIG. 3B shows antibodies to recombinant δ-giardin followed by Alexa Fluor 633

(red)-conjugated secondary antibodies. FIGS. 3C and 3D show images of a permeabilized trophozoite double-labeled with antibodies against recombinant δ- and β-giardin, respectively. Scale bar=5 µm.

FIGS. 4A and 4D depict fluorescence; FIGS. 4B and 4E depict differential interference contrast (DIC); and FIGS. 4C and 4F depict overlay of fluorescence with DIC images. Scale bar=5 µm.

FIGS. 5C and 5D depict G. lamblia trophozoites and cysts, respectively, labeled with MAb 5E11.

FIGS. 6-1A, B, C, D) to the dorsal side (bottom panels: FIGS. 6-7A, B, C, D) of the trophozoite. Red-channel fluorescence images (FIGS. 6-1A, 6-2A, 6-3A, 6-4A, 6-5A, 6-6A, 6-7A) and green-channel fluorescence images (FIGS. 6-1B, 6-2B, 6-3B, 6-4B, 6-5B, 6-6B, 6-7B) show the level of immunoreactivity for δ- and β-giardin respectively. Multi-channel (red and green overlay) fluorescence images (FIGS. 6-1C, 6-2C, 6-3C, 6-4C, 6-5C, 6-6C, 6-7C) show co-localization of δ- and β-giardins with yellow pixels. Only pixels within the outlined area were used in quantitative co-localization. Scatter plots (FIGS. 6-1D, 6-2D, 6-3D, 6-4D, 6-5D, 6-6D, 6-7D) show the distribution of florescence signal (immunoreactivity) between two channels together with the number of co-localized pixels (area 3) for every optical section. A heat map on the right shows the absolute frequency of pixels in scatter plots. Scale bar=5 µm.

FIG. 7 shows Co-localization analysis of β- and δ-giardins within seven representative optical sections of Giardia lamblia ventral disc (FIGS. 7-1A, B, C, D-FIGS. 7-7A,B,C, D). Optical sectioning was conducted from the ventral side (top panels: FIGS. 7-1A, B, C, D) to the dorsal side (bottom panels: FIGS. 7-7A, B, C, D) of the disc. Red-channel fluorescence images (FIGS. 7-1A, 7-2A, 7-3A, 7-4A, 7-5A, 7-6A, 7-7A) and green-channel fluorescence images fluorescence images (FIGS. 7-1B, 7-2B, 7-3B, 7-4B, 7-5B, 7-6B, 7-7B) show the level of immunoreactivity for δ- and β-giardin, respectively. Multi-channel (red and green overlay) fluorescence images (FIGS. 7-1C, 7-2C, 7-3C, 7-4C, 7-5C, 7-6C, 7-7C) show co-localization of δ- and β-giardin with yellow pixels. Scatter plots (FIGS. 7-1D, 7-2D, 7-3D, 7-4D, 7-5D, 7-6D, 7-7D) show the distribution of florescence signal (immunoreactivity) between two channels together with the number of co-localized pixels (area 3) for every optical section. A heat map on the right shows the absolute frequency of pixels in scatter plots. Scale bar=2 µm.

FIG. 8A depicts spatial localization of δ-giardin as red fluorescence and that of β-giardin (FIG. 8B) as green fluorescence. FIG. 8C shows the spatial localization of both giardins, δ and β. FIG. 8D depicts a section through the disc and shows δ- and β-giardin colocalization as yellow pixels

DETAILED DESCRIPTION OF THE INVENTION

Figure 1:
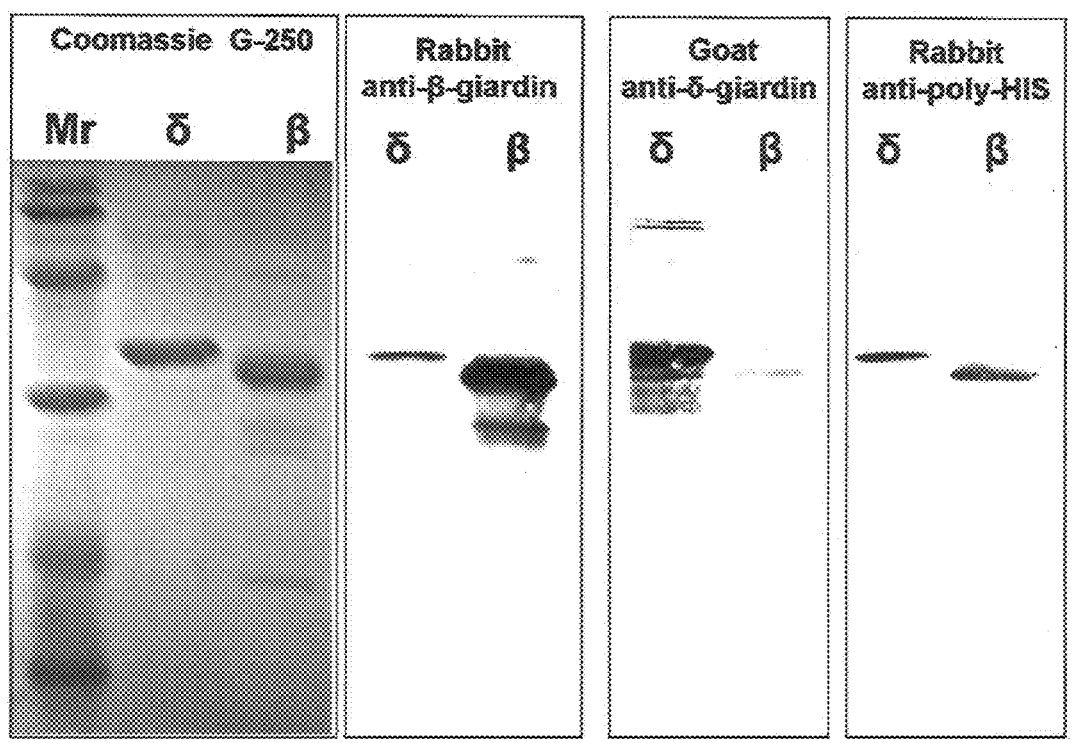
FIG. 1 depicts SDS-PAGE/immunoblotting analysis of recombinant β- and δ-giardins. Panel 1, Coomassie Blue staining, Panels 2-6, immunostaining with specific antisera. Panel 2, rabbit anti-β-giardin; Panel 3, rabbit anti-δ-giardin; Panel 4, goat anti-δ-giardin; Panel 5, rabbit anti-irrelevant polyHis protein; Panel 6, goat anti-irrelevant polyHis protein.

We have determined the relative location of δ- and β-giardins within the Giardia lamblia ventral disc in the trophozoite stage of Giardia. For in-depth analysis of β- and δ-giardin localization within the ventral disc, methanol-fixed trophozoites were double-labeled with antibodies against recombinant β- and δ-giardin, and then subjected to high-resolution scanning along the Z axis. Scanning of the multiple focal planes of entire trophozoites or of ventral disc alone identified specific immunoreactivity for each giardin within the ventral disc. Seven representative optical sections (from 54 acquired) of a trophozoite demonstrate different degrees of co-localization of β- and δ-giardin in the ventral disc along the Z axis. Scatter plots show the quantitative distribution of florescence signal (intensity) between two channels (β-giardin green and δ-giardin red) together with the number of co-localized pixels for each optical section presented. The disc areas, in which β- and δ-giardin are co-localized, are also shown for every optical section.

The results of the quantitative co-localization as well as single- and multi-channel confocal images demonstrate the gradual shift in the intensity of immunoreactivity for β- and δ-giardin. For δ-giardin, a higher intensity was observed between mid-section and the ventral side of the ventral disc. In contrast, higher intensity of immunoreactivity for β-giardin was localized between the mid-section and dorsal side of the ventral disc. This pattern of β- and δ-giardin distribution within the ventral disc is also was confirmed by two independent quantitative parameters of co-localization: Pearson's Correlation coefficient and Mander's Overflap coefficient.

A three-dimensional (3D) representation of the spatial localization of β- and δ-giardins to the ventral disc, positioned with the ventral side upwards, was generated using AxioVision 4-D software. Spatial localization of both δ- and β-giardin within the ventral disc, revealed δ-giardin on the ventral side and β-giardin on the dorsal side. An identical localization of β- and δ-giardins was observed in a dye swap experiment, demonstrating that distribution of the immunoreactivity for β- and δ-giardins was not affected by the spectral properties of the fluorophores.

The present immunofluorescence-based localization study is consistent with earlier reports that identified β-giardin associated with the ventral disc (Crossley and Holberto, supra; Holberton and Ward, supra). This study demonstrated for the first time that δ-giardin, even though it shares a great degree of co-localization with β-giardin, is present more ventrally and therefore is closest to the side of the ventral disc that makes contact with host cells.

The purpose of the present study was to express recombinant G. lamblia δ-giardin protein, produce antisera and monoclonal antibodies specific for recombinant δ-giardin and also for β-giardin and use the antisera and the MAbs to localize the native δ-giardin protein and the native identified β-giardin in the ventral disc of G. lamblia trophozoites.

As used herein, unless otherwise specifically noted, "δ-giardin" refers to all forms of δ-giardin which are useful in the compositions and/or methods of the invention, including isolated unmodified native or recombinant G. lamblia δ-giardin, or a modified form (variant) or fragment thereof. Recombinant δ-giardin of the invention is identified by SEQ ID NO: 2. The invention encompasses DNA sequences which encode peptides having amino acid sequences that are homologous to that of SEQ ID NO: 2.

"Homologous" peptides are defined herein as peptides having an amino acid sequence sufficiently duplicative of δ-giardin to be antigenic and capable of eliciting antibodies which specifically and selectively bind to δ-giardin. DNA sequences encoding δ-giardin with the amino acid sequence identified by SEQ ID NO:2 and DNA sequences which encode homologous proteins and which also hybridize to the DNA sequence identified by SEQ ID NO:1 (or its complement) under stringent conditions are particularly preferred.

As used herein, unless otherwise specifically noted, "β-giardin" refers to all forms of β-giardin which are useful in the compositions and/or methods of the invention, including isolated unmodified native or recombinant *G. lamblia*-giardin, or a modified form (variant) or fragment thereof. Recombinant β-giardin of the invention is identified by SEQ ID NO: 4. The invention encompasses DNA sequences which encode peptides having amino acid sequences that are homologous to that of SEQ ID NO: 4. "Homologous" peptides are defined herein as peptides having an amino acid sequence sufficiently duplicative of β-giardin to be antigenic and capable of eliciting antibodies which specifically and selectively bind to β-giardin. DNA sequences encoding β-giardin with the amino acid sequence identified by SEQ ID NO:4 and DNA sequences which encode homologous proteins and which also hybridize to the DNA sequence identified by SEQ ID NO:3 (or its complement) under stringent conditions are particularly preferred.

Further, because of the degeneracy of the genetic code, there exists a finite set of nucleotide sequences which can code for a given amino acid sequence. It is understood that all such equivalent sequences are operable variants of the disclosed sequence, since all give rise to the same protein (i.e., the same amino acid sequence) during in vivo transcription and translation, and are hence encompassed by the instant invention.

The present invention also encompasses δ-giardin and β-giardin variants. A "variant" of δ-giardin may have an amino acid sequence that is different by one or more amino acid "substitutions". The variant may have "conservative substitutions", wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software. The term "biological activity" refers to recombinant δ-giardin and/or β-giardin having structural, regulatory or biochemical functions of the naturally occurring δ-giardin and β-giardin.

The term "antibody," as used herein, includes, but is not limited to a polypeptide substantially encoded by an immunoglobulin gene or immunoglobulin genes, or fragments thereof which specifically bind and recognize an anatyte (antigen). Examples include polyclonal, monoclonal, chimeric, humanized, CDR-grafted, and single chain antibodies, and the like. Fragments of immunoglobulins, including Fab, Fab', F(ab')$_2$ and F(v) fragments and fragments produced by an expression library, including phage display. See, e.g., Paul, Fundamental Immunology, Third Ed., 1993, Raven Press, New York, for antibody structure and terminology.

Recombinant δ-giardin and β-giardin can be used as immunogens to generate monoclonal and polyclonal antibodies that are selectively specific for native and recombinant δ-giardin and β-giardin. In addition, a number of companies and institutions offer services that produce antibodies against the desired antigen (e.g., a protein supplied by the customer or a peptide synthesized to order). A general method of preparing the antibodies of the invention is described below. Those skilled in the art will recognize that the present invention, including the MAbs and hybridoma cell lines described herein, provide a variety of ways to make the specific antibodies of the present invention. Monoclonal antibodies which specifically bind to recombinant δ-giardin and β-giardin were custom made using recombinant δ-giardin and β-giardin provided by Applicant (Hybridoma Core Facility, Lerner Research Institute, Cleveland Clinic Foundation; Retrieved from the Internet: lerner.ccf.org).

To prepare antibodies, a host animal is immunized using the recombinant δ-giardin and β-giardin proteins as the immunogens. The host serum or plasma is collected following an appropriate time interval to provide a composition comprising antibodies reactive with the immunogen. Monoclonal antibodies to a specific antigen may be produced by immunizing mice several times over 1-2 months with a protein, then isolating spleen cells from the immunized mice, and carrying out a cell fusion between these spleen cells and mouse myeloma cells. The resulting hybridomas are cultivated in vitro, and culture supernatant overlying the hybridomas are screened for the production of monoclonal antibodies that react with the immunizing protein. Methods of antibody (polyclonal and monoclonal) production and isolation are well known in the art. See, for example, Harlow et al. 1988, supra, or Coligan et al. (Eds) (1999) *Current Protocols in Immunology*, Wiley Interscience, NY. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-antibody.

The phrases "specifically binds to" or "specifically immunoreactive with", when referring to an antibody or other binding moiety refers to a binding reaction which is determinative of the presence of the target analyte in the presence of a heterogeneous population of proteins and other biologics. Thus, under designated assay conditions, the specified binding moieties bind preferentially to a particular target analyte and do not bind in a significant amount to other components present in a test sample. Specific binding to a target analyte under such conditions may require a binding moiety that is selected for its specificity for a particular target analyte. A variety of immunoassay formats may be used to select antibodies specifically immunoreactive with a particular protein. For example, solid-phase ELISA immunoassays are routinely used to select monoclonal antibodies specifically immunoreactive with an analyte. See Hartow and Lane (1988) Antibodies, A Laboratory Manual, Cold Spring Harbor Publications, New York, for a description of immunoassay formats and conditions that can be used to determine specific immunoreactivity. Typically a specific or selective reaction will be at least twice background signal to noise and more typically more than 10 to 100 times background.

The term "peptide" as used herein refers to a molecular chain of amino acids with a biological activity (e.g., capable of binding antibody specific for δ-giardin or β-giardin), and does not refer to a specific length of the product. Thus, inter alia, proteins, oligopeptides, polypeptides and fusion proteins as well as fusion peptides are included. Further, δ-giardin and recombinant δ-giardin are interchangeable as reagents for detecting δ-giardin-specific antibodies, for generating δ-giardin-specific antibodies, and for vaccine development. Similarly, β-giardin and recombinant β-giardin are interchangeable as reagents for detecting β-giardin-specific antibodies, for generating β-giardin-specific antibodies, and for vaccine development. Thus, inter alia, references to δ- or β-giardin encompass recombinant δ- or β-giardin, respectively, and references to recombinant δ- or β-giardin encompass δ- or β-giardin, respectively.

A nucleotide sequence (SEQ ID NO: 1) encoding recombinant δ-giardin is utilized to provide the recombinant δ-giardin. DNA sequences which are substantially homologous to the nucleotide sequence of SEQ ID NO:1 are also encompassed by the invention. As defined herein, two DNA sequences are substantially homologous when at least 85% (preferably at least 90% and most preferably 95%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al. 1989. Molecular Cloning: A Laboratory Manual, Cold Spring Harbor Laboratory, Cold Spring, N.Y., or DNA Cloning: A Practical Approach, Vol. I and II (Ed. D. N. Glover), IRL Press, Oxford, 1985. Sambrook et al. describe highly stringent conditions as a hybridization temperature 5-10EC below the $T_m$ of a perfectly matched target and probe; thus, sequences that are "substantially homologous" would hybridize under such conditions.

The DNA sequences can be used to prepare recombinant DNA molecules by cloning in any suitable vector. A variety of vector-host combinations may be employed. Host cells may be either prokaryotic or eukaryotic, and, when the host cells are bacterial cells, they may be either gram-negative or gram-positive bacteria. In general, vectors containing nucleic acids encoding δ-giardin can be utilized in any cell, either eukaryotic or prokaryotic, including mammalian cells (e.g., human (e.g., HeLa), monkey (e.g., COS), rabbit (e.g., rabbit reticulocytes), rat, hamster (e.g., CHO and baby hamster kidney cells) or mouse cells (e.g., L cells), plant cells, yeast cells, Sf9 or Sf21 insect cells (*Spodoptera frugiperda*), or bacterial cells (e.g., *E. coli*)). However, bacterial vectors and host cells are preferred.

Nucleic acids encoding the δ-giardin can be introduced into a vector such as a plasmid, cosmid, phage, virus, viral particle or mini-chromosome and inserted into a host cell or organism by methods well known in the art. The vectors which can be utilized to clone and/or express these nucleic acids are the vectors which are capable of replicating and/or expressing the nucleic acids in the host cell in which the nucleic acids are desired to be replicated and/or expressed. See, e.g., F. Ausubel et al. 1992. Current Protocols in Molecular Biology, Greene Publishing Associates and Wiley-Interscience and Sambrook et al. (1989) for examples of appropriate vectors for various types of host cells.

Within each specific vector, various sites may be selected for insertion of the isolated DNA sequence. These sites are usually designated by the restriction enzyme or endonuclease that cuts them. For example, in pBR322, the Pst I site is located in the gene for penicillinase between the nucleotide triplets that code for amino acids 181 and 182 of the penicillinase protein.

The antigenic peptides of the invention are produced by growing host cells transformed by the expression vectors described above under conditions whereby the antigen is produced. The antigens are then isolated from the host cells. The selection of the appropriate growth conditions and recovery methods are well within the skill of the art. Host bacterial cells may be chosen that are mutated to be reduced in or free of proteases, so that the proteins produced are not degraded. A recombinant δ-giardin protein has been produced in the pET28c expression vector. Plasmid pET28C- δ-giardin was transformed into competent cell *E. coli* strain BL21(DE3).

An antibody of the present invention in one embodiment is characterized as comprising antibody molecules that immunoreact with *G. lamblia* δ-giardin. An antibody of the present invention is typically produced by immunizing a mammal with an immunogen or vaccine containing a *G. lamblia* δ-giardin to induce, in the mammal, antibody molecules having immunospecificity for the immunizing δ-giardin.

The antibody of the present invention may be contained in blood plasma, serum, hybridoma supernatants and the like. Alternatively, the antibodies of the present invention are isolated to the extent desired by well-known techniques such as, for example, ion exchange chromatography, sizing chromatography, or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibodies of the IgG class are preferred for purposes of passive protection. The antibodies can be measured in standard immunoassay protocols. Such assays include, but are not limited to, agglutination assays, radioimmunoassays, enzyme-linked immunosorbent assays, fluorescence assays, Western blots and the like. The antibodies of the present invention are also useful in prevention of infections and diseases caused by *G. lamblia*.

Also part of this invention is a composition that comprises the antibodies of this invention; and a carrier, preferably a physiologically and/or pharmaceutically tolerable (acceptable) carrier. Carriers function to dilute the active ingredients and facilitate application to the intended surface and are typically aqueous carriers such as water, buffered aqueous solutions, aqueous alcoholic mixtures, and the like. Compositions comprising carriers that are for pharmaceutical use, particularly for use in mammals, comprise a carrier that is pharmaceutically-acceptable. Depending on the intended mode of administration, the compounds of the present invention can be in various pharmaceutical compositions. The compositions will include, as noted above, an effective amount of the selected immunogen and/or antibody of the invention in combination with a pharmaceutically acceptable carrier and, in addition, may include other medicinal agents, pharmaceutical agents, carriers, adjuvants, diluents, excipients, etc. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe. Likewise, ingredients may be selected for any given composition which are cooperative in their combined effects whether incorporated for antimicrobial efficacy, physical integrity of the formulation or to facilitate healing and the health of the host. By "pharmaceutically acceptable" is meant a material that is not biologically or otherwise undesirable, i.e., the material may be administered to an individual along with the immunogen and/or antibody or other composition without causing any undesirable biological effects or interacting in a deleterious manner with any of the other components of the pharmaceutical composition in which it is contained. Examples of such carriers are known in the art and need therefore not be provided herein.

The pharmaceutical compositions of this invention contain a pharmaceutically and/or therapeutically effective amount of the antibody of the invention.

The δ-giardin or other agents of this invention, as well as antibodies and other necessary reagents and appropriate devices and accessories, may be provided in kit form so as to be readily available and easily used.

Also part of this invention is a method of diagnosing *Giardia* infection, that comprises contacting a body substance with an anti-δ-giardin antibody of this invention; and detecting any selective binding of the antibody to any antigenic δ-giardin peptides present in the body substance. The anti-δ-giardin antibodies may be monoclonal or polyclonal. The detection of the antibody-polypeptide complex may be conducted by any method known in the art. This includes solid phase, double antibody, sandwich double antibody, and triple antibody assays, and the like, including radioimmunoassay, enzyme-linked immunosorbent assay, fluorescent assay, including flow cytometry, chemiluminescent assay, competitive immunoassay, membrane-based immunoassay, immunomagnetic separation, precipitation, agglutination, antigen capture, or the like.

The successful cloning and expression of recombinant δ-giardin and the generation of antisera specific for recombinant δ-giardin was a major step in localizing the protein in *G. lamblia* trophozoites. Antibodies that specifically bind to δ-giardin can specifically identify the presence of *G. lamblia* trophozoites and thus be a diagnostic agent for identifying a *G. lamblia* infection. Antibodies that specifically bind to δ-giardin can specifically inhibit or prevent in vitro attachment of trophozoites to host cells.

EXAMPLES

Having now generally described this invention, the same will be better understood by reference to certain specific examples, which are included herein only to further illustrate the invention and are not intended to limit the scope of the invention as defined by the claims.

Example 1

*Giardia lamblia*

*Giardia lamblia* (WB strain assemblage A) trophozoites were cultured in modified TYI-S-33 media (Keister, D. B. 1983. *Transactions Royal Soc. Tropical Med. Hygiene* 77: 487-488 in 15-ml sterile polypropylene tubes at 37° C. *Giardia lamblia* were grown in continuous culture by inoculating 12 ml of new media every 2-3 days with approximately 5×10$^5$ trophozoites from a viable culture.

Example 2

Real Time-Polymerase Chain Reaction (RT-PCR), Cloning and Purification of Giardins Cloning and purification of recombinant δ-giardin was conducted as described (Jenkins et al., supra). Recombinant β-giardin was produced by first amplifying the respective cDNA by RT-PCR using primers (Table 1) derived from DNA sequences for beta-giardin (X07919, ORF-frame 3). In brief, 1 ng of total RNA was subjected to real-time RT-PCR using 1 pmole of β-Forward and Reverse primers, and the Superscript III One-Step RT-PCR system (Invitrogen, Carlsbad, Calif.) in a 25-μl reaction volume. RT-PCR consisted of reverse transcription at 47° C. for 1 hr, denaturation at 94° C. for 1 min, followed by 35 cycles of 94° C. for 30 sec, 59° C. for 30 sec, 72° C. for 1 min, and a final extension at 72° C. for 5 min.

TABLE 1

Primer sequences used in the cloning of cDNA coding for *G. lamblia* β-giardin protein

| Primer Name | Primer Sequence (5'-3') | SEQ ID NO: |
|---|---|---|
| Beta-Forward | AATTT<u>GGTACC</u>ATGGACAAGCCCGACGA | 5 |
| Beta-Reverse | GGG<u>TTCGAA</u>TTAGTGCTTTGTACC | 6 |

Underlined sequence refers to restriction enzyme recognition site.
Beta-Forward: KpnI; Beta-Reverse: HindIII RT-PCR products were purified using a PCR purification kit (Qiagen, Valencia, Calif.), and eluates were ethanol precipitated, dried at room temperature, and suspended in 10 μl of sterile H$_2$O, followed by KpnI and HindIII digestion using standard procedures (Sambrook et al. 1989. In: *Molecular Cloning: A Laboratory Manual*. Cold Spring Harbor Laboratory Press, New York). The expression vector pTrcHisB (Invitrogen) was also digested with the identical enzymes. After digestion at 37° C. for 2 h, both β-giardin RT-PCR product and pTrcHisB were subjected to agarose electrophoresis, visualized by EtBr staining, excised from the gel, and purified using a gel purification kit (Qiagen) and ligated overnight at 15° C. using T4 DNA ligase (New England Biolabs, Ipswich, Mass.). The ligation mixtures were transformed into *Escherichia coli* DH5 cells according to standard procedures (Hanahan, D. 1983. *J. Mol. Blol.* 166:557-580) and recombinant β-giardin clones were identified by colony PCR (Güssow and Clackson et al. 1989. *Nucleic Acids Res.* 17:4000) using pTrcHis-specific primers (pTrcHis-Forward 5' CTG TAC GAC GAT GAC GAT AAG 3'; SEQ ID NO: 7 and pTrcHis-Reverse 5' TCA TCC GCC AAA ACA GCC AAG; SEQ ID NO: 8). The reading frame and orientation of the cDNAs were confirmed by DNA sequencing of at least three recombinant plasmids using a pTrcHis-universal primer (5' CGATTAAATAGAGG 3'; SEQ ID NO: 9) and a Big Dye Terminator v3.1 Cycle Sequencing Kit (Applied Biosystems, Carlsbad, Calif.). Sequencing reactions were run on an ABI373, analyzed using Sequencher 4.9 software (GeneCodes Corp., Ann Arbor, Mich.).

For high level expression, recombinant pTrcHis-β giardin plasmid DNA was transformed into *E. coli* BL21 (Novagen, San Diego, Calif.). Cultures were grown in LB medium containing 100 μg/ml ampicillin (Sigma Chemical Co., St. Louis, Mo.) at 37° C. until O.D.=0.5, whereupon expression of recombinant β-giardin was induced by the presence of 1 mM isopropylthiocyanate (IPTG, Sigma). The cultures were harvested after 4 h IPTG induction by centrifugation at 3,000 g for 10 min. The cell pellets were extracted with native binding buffer (Invitrogen, Carlsbad, Calif.) containing PMSF protease inhibitor (Sigma), frozen-thawed 2 times between a dry-ice ethanol bath and a 37° C. water bath, and sonicated twice for 15 s each, with incubation on wet ice for 1 min between sonications. The protein extracts were treated with 1 U/ml RNase and DNase for 30 min at room temperature and pelleted by centrifugation at 5,000 g for 30 min. The insoluble pellet was extracted by suspension in denaturing binding buffer (Invitrogen) for 30 min at room temperature on a rocker. The extracts were pelleted by centrifugation at 5,000 g for 30 min, and the supernatant subjected to NiNTA affinity chromatography to purify recombinant β-giardin protein.

Example 3

Preparation of Antibodies

Polyclonal sera specific for β-giardin was prepared by a commercial company (Pacific Immunology, Inc., Ramona, Calif.) by immunizing two New Zealand White rabbits with 100 μg/injection of NiNTA-purified recombinant β-giardin emulsified in complete Freunds adjuvant (CFA, primary immunization) or incomplete Freunds adjuvant (ICFA, 3 booster immunizations). Polyclonal sera specific for δ-giardin was prepared by the same company (Pacific Immunology) by immunizing 1 goat with 200 μg/injection of NiNTA-purified recombinant δ-giardin in CFA (primary immunization) or ICFA (3 booster immunizations).

Rabbits were killed by exsanguination, and blood processed for serum following protocols approved by the BARC Animal Care and Use Committee. Preliminary studies showed that anti-β-giardin titers were similar in both rabbits, and thus sera were pooled for use in all assays described below.

One monoclonal antibody (MAb) was isolated which specifically binds to the recombinant δ-giardin; and one MAb was identified which reacted specifically with recombinant β-giardin (Hybridoma Core Facility, Lerner Research Institute, Cleveland Clinic Foundation). The MAb 5E11-19 which specifically binds to native and recombinant δ-giardin and the MAb 2G9-11 which specifically binds to native and recombinant β-giardin were selected for further study based on their reactivity by immunofluorescence and immunoblotting assay with native Giardia lamblia protein. The hybridoma cell line 2G9-11 deposited at ATCC as PTA-12047 produces the IgG MAb 2G9-11 which specifically binds to native and recombinant β-giardin. The hybridoma cell line 5E11-19 deposited at ATCC as PTA-12048 produces the IgM MAb 5E11-19 which specifically binds to native and recombinant δ-giardin.

Example 4

Immunoblotting Analysis

Recombinant δ- or β-giardin protein was fractionated by SDS-polyacrylamide gel electrophoresis followed by transblotting to Immobilon membrane (Millipore, Billerica, Mass.) in a semi-dry transblotter apparatus (BioRad, Hercules, Calif.). After transfer, the membranes were treated with PBS containing 2% non-fat dry milk (PBS-NFDM) to block non-specific immunoglobulin binding in subsequent steps. After blocking, the membranes were incubated with either rabbit anti-recombinant β-giardin or goat anti-δ-giardin sera or antisera to an irrelevant polyHis-fusion protein (1:1000 dilution) for 2-4 h at room temp (RT) on a laboratory shaker, followed by 2 h incubation with biotinylated goat-anti-rabbit IgG or biotinylated rabbit anti-goat IgG (1:1,000 dilution) (Sigma), and 1 h with avidin-peroxidase (Sigma, 1:5,000 dilution). All antibodies were diluted in PBS containing 0.05% Tween 20 (PBS-TW), and removed after each step by 3 washes with PBS-TW. Binding of anti-giardin antibodies was assessed by a final incubation with peroxidase substrate-0.5 mg/ml 4-chloro-1-napthol (Sigma) and 0.015% $H_2O_2$ (Sigma) in PBS.

Immunoblotting analysis of goat anti-δ-giardin or rabbit anti-β-giardin sera showed that polyclonal antibodies specifically recognized the corresponding recombinant giardin (FIG. 1). Faint recognition of δ-giardin observed with rabbit anti-β-giardin sera was similar to that observed with rabbit antisera prepared against an irrelevant recombinant polyHis fusion protein (FIG. 1). Also, goat antisera to an irrelevant recombinant polyHis fusion protein showed slight recognition of both recombinant β- and δ-giardins which may reflect binding of a common polyHis portion of recombinant proteins (FIG. 1).

Figure 2:
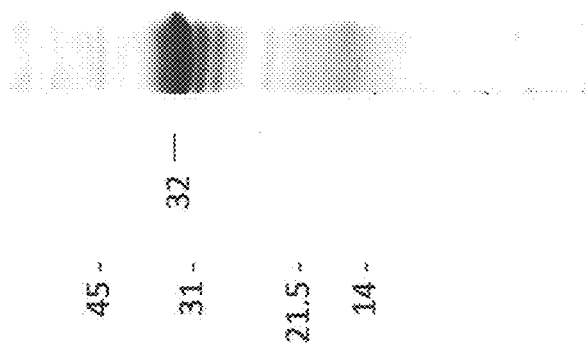
FIG. 2 depicts a Western Blot analysis of recombinant β-giardin using the monoclonal antibody (MAb) 2G9.

Western blot analysis with the anti-β-giardin MAb 2G9 reacted with a 31 kDa protein in G. lamblia trophozoites (FIG. 2). The anti-δ-giardin MAb 5E11, an IgM, specifically binds to δ-giardin (data not shown).

Example 5

Immunofluorescence Staining

Prior to immunofluorescence staining, G. lamblia trophozoites were either treated with paraformaldehyde (PF) to retain integrity of the plasma membrane (EI-Kon at al. 2009) or were air-dried onto multi-well glass slides. In the former, G. lamblia trophozoites were treated in with 3% PF in PBS for 5 min at RT, followed by 3 washes with PBS, and treatment for 30 min with 2% PBS-NFDM to reduce non-specific binding in subsequent steps. Staining was accomplished by incubating $10^4$ trophozoites for 1 h in a 100 μl suspension of 1:1000 dilution of rabbit anti-recombinant β-giardin or goat anti-δ-giardin sera followed by a 1 h incubation with 100 μl fluorescein isothiocyanate (FITC) goat anti-rabbit IgG (Sigma) or Alexa Fluor 633-conjugated donkey anti-goat IgG (Invitrogen) diluted to 20 μg/ml. Antibodies were removed between incubations by washing trophozoites 3 times in PBS followed by centrifugation for 1 min at 3,000 g.

Immunofluorscence staining on slides was conducted by first pipetting $10^4$ trophozoites in individual wells of multi-well slides (Erie Scientifc Co., Portsmouth, N.H.) and allowing the parasites to air dry at RT for 1 h. The slides were then either used directly or treated with methanol for 5 min followed by gentle rinsing in PBS. After drying, the multi-well slides containing trophozoites were stored at −70° C. Just prior to immunofluorescence staining of trophozoites, the slides were removed from the freezer and allowed to warm to RT.

Non-specific binding of antibodies was blocked by the treatment of each well with PBS-NFDM for 30 min at RT. The slides were gently rinsed with PBS, allowed to air-dry, and then incubated singly or in combination with a 1:1000 dilution of goat anti-δ-giardin sera or rabbit anti-β-giardin sera. The slides were incubated in a humidified chamber for 1 h at RT, and then gently rinsed 3 times with PBS and allowed to air dry, followed by staining with either FITC-conjugated rat anti-rabbit IgG (Sigma) or Alexa Fluor 633-conjugated donkey anti-goat IgG (Invitrogen). In order to avoid cross-reactivity of secondary antibodies, Alexa Fluor 633-conjugated donkey anti-goat IgG was applied in one step, and the FITC goat anti-rabbit IgG was applied in a second step. To observe if Alexa Flour 633 or FITC spectral properties can affect spatial distribution of giardins immunoreactivity a dye swap experiment was conducted wherein FITC mouse anti-goat IgG (Sigma) was followed by Alexa Fluor 633-conjugated goat anti-rabbit IgG (Invitrogen) after incubation with primary anti-δ-giardin and anti-β-giardin sera. After the final incubation, the slides were gently rinsed with PBS, allowed to air dry, and then overlaid with 5 μl/well of Vectashield mounting medium (Vector Laboratories, Burlingame, Calif.) and a glass coverslip.

For analysis with the MAbs 2G9 and 5E11, non-specific binding of the MAbs was blocked by the treatment of each well with PBS-NFDM for 30 min at RT. The slides were gently rinsed with PBS, allowed to air-dry, and then incubated singly or in combination with MAb at 5 mg/ml in PBS/1% BSA/0.1% sodium azide in a humidified chamber for 1 h at RT, and then gently rinsed 3 times with PBS and allowed to air dry, followed by staining with either FITC-conjugated goat anti-mouse IgG (Sigma) or FITC-conjugated goat anti-mouse IgM (Invitrogen). After the final incubation, the slides were gently rinsed with PBS, allowed to air dry, and then overlaid with 5 μl/well of Vectashield mounting medium (Vector Laboratories, Burlingame, Calif.) and a glass coverslip.

Example 5

Immunolocalization Analysis

A Zeiss 710 laser scanning confocal microscopy (LSCM) system was utilized in immunolocalization analysis. The images were observed using a Zeiss Axio Observer inverted microscope with 63× and 100×1.4 NA oil immersion Plan Apochromatic objectives. A photomultiplier tube captured in a single-track mode the specimen fluorescence excited by: (1) a 488-mn green laser and emitted fluorescence passing through an FITC filter with limits set between 510-535 nm, for detection of FITC-conjugated antibodies or (2) a 633 nm red laser passing through an MBS-488/561/633 filter with limits set between 638-747 nm for detection of Alexa Fluor 633-conjugated antibodies. Zeiss Zen™ 2008 software was used to obtain the images with 1024×1024 and 2048×2048 pixel resolution and Z stacks ranging from 22 to 60 focal planes. Zeiss AxioVision version 4.8.3 with 4D software was used to construct three-dimensional (3D) images of specimens. Colocalization module integrated in Zeiss Zen™ 2008 software was used to generate scatter plots and calculate colocalization coefficients.

Figure 3:
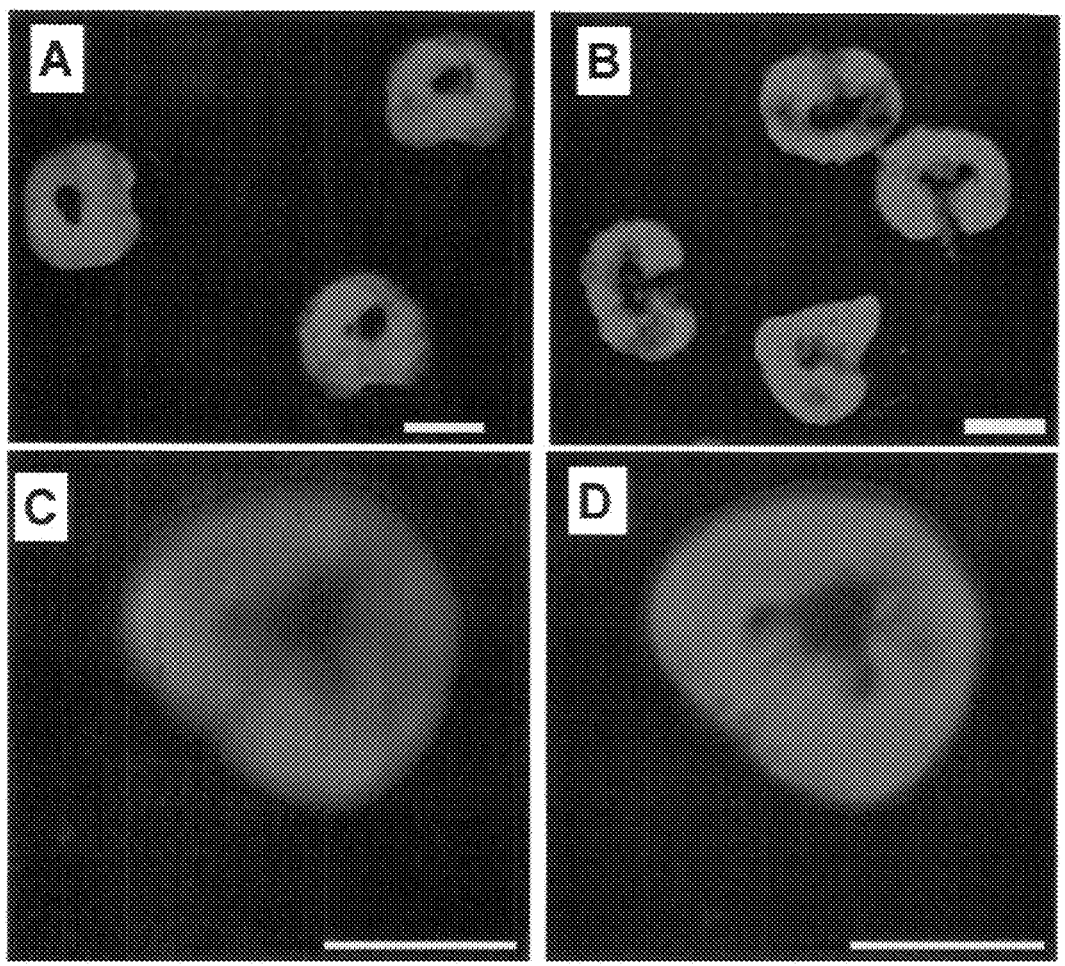
FIGS. 3A-3D show fluorescence microscopy images of methanol-fixed *Giardia lamblia* trophozoites singly labeled with antibodies against β- and δ-giardin.
Figure 4:
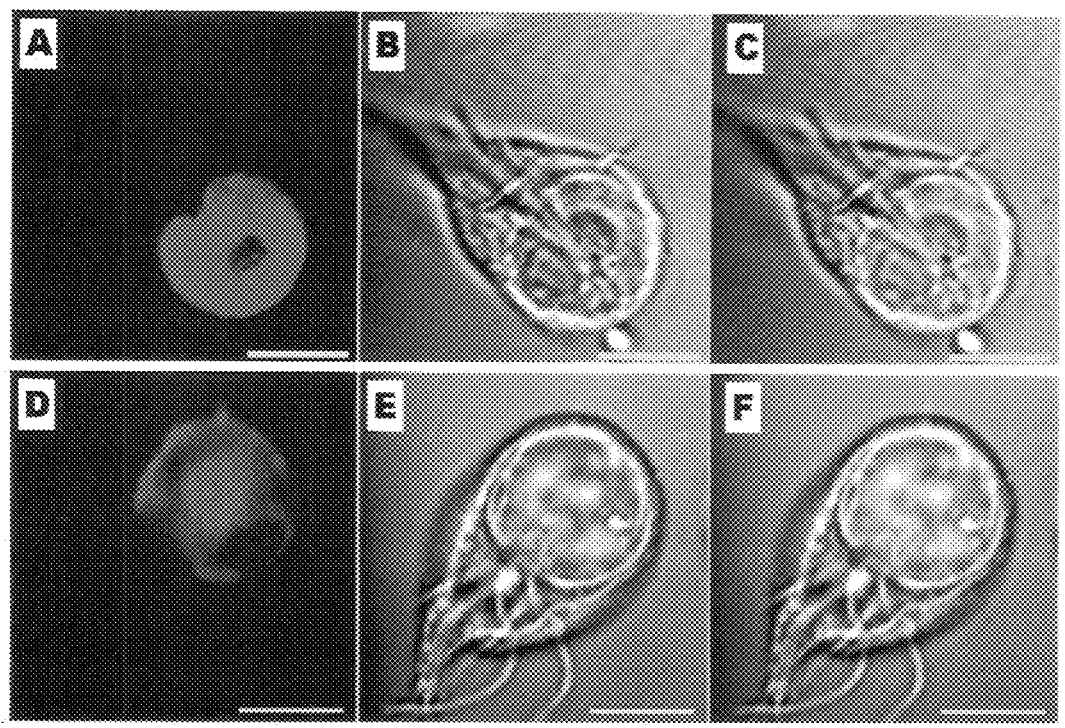
FIGS. 4A-4F show laser scanning confocal microscopy (LSCM) images of the ventral side of paraformaldehyde-fixed Giardia lamblia trophozoites labeled with antibodies against β-giardin (FIGS. 4A, 4B, 4C) or δ-giardin (FIGS. 4D, 4E, 4F).
Figure 5A:
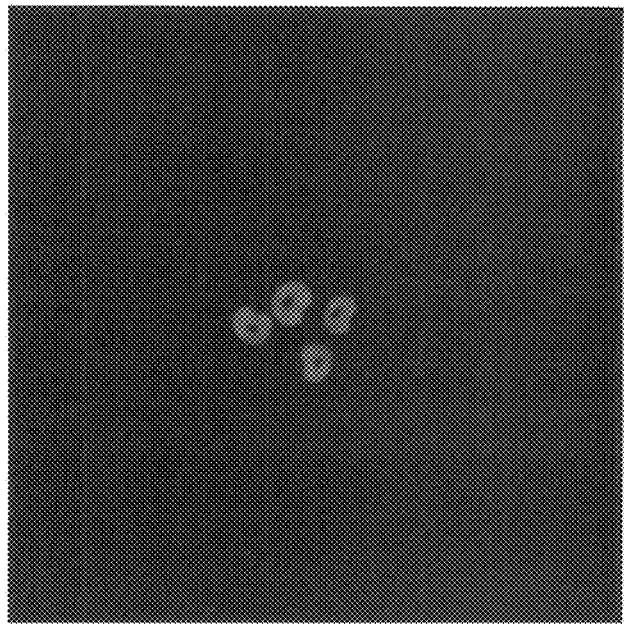
FIGS. 5A-5D depict immunofluorescence analysis (IFA) of air-dried Giardia lamblia trophozoites and cysts singly labeled with monoclonal antibodies specific for β-giardin (2G9) or δ-giardin (5E11). G. lamblia trophozoites (FIG. 5A) and cysts (FIG. 5B) are shown labeled with MAb 2G9.
Figure 5B:
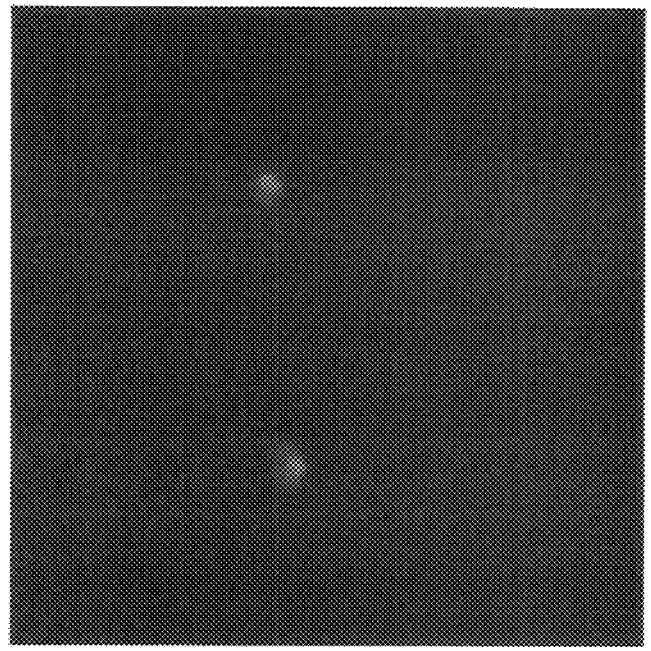
Figure 5C:
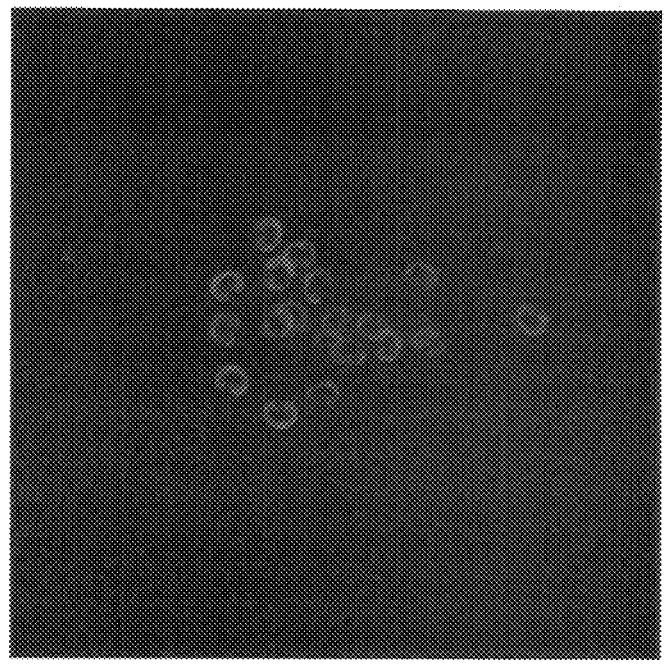
Figure 5D:
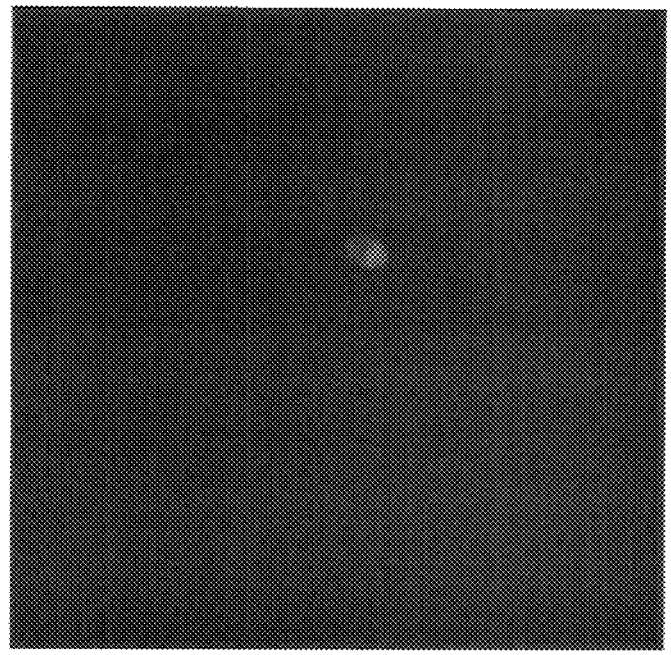

In methanol-fixed, permeabilized trophozoites that were singly labeled and subjected to LSCM analysis, antibodies to recombinant β- and δ-giardin localized to the ventral disc (FIG. 3A,B). In permeabilized trophozoites double-labeled with antibodies against recombinant β- and δ-giardin both antigens appear to be present only in association with the ventral disc, as staining outside of the ventral disc was negligible (FIG. 3C, D). Although slightly more intense, the recognition pattern of β-giardin in non-permeabilized (PF-fixed) trophozoites was similar to that observed with permeabilized (methanol-fixed) parasites (FIG. 4A-C). However, anti-δ-giardin staining of non-permeabilized trophozoites produced a more diffuse labeling compared to that observed with permeabilized trophozoites (FIG. 4D-F). While peripheral staining of the ventral disc was observed, δ-giardin appeared to be concentrated in the center of the disc in non-permeabilized trophozoites. This data suggest that both β- and δ-giardin are associated with the plasma membrane.

MAb 2G9 (specific for (β-giardin) and MAb 5E11 (specific for δ-giardin) react with both trophozoites and cysts that have been air-dried onto multi-well glass slides (FIG. 5A-D).

Figure 6:
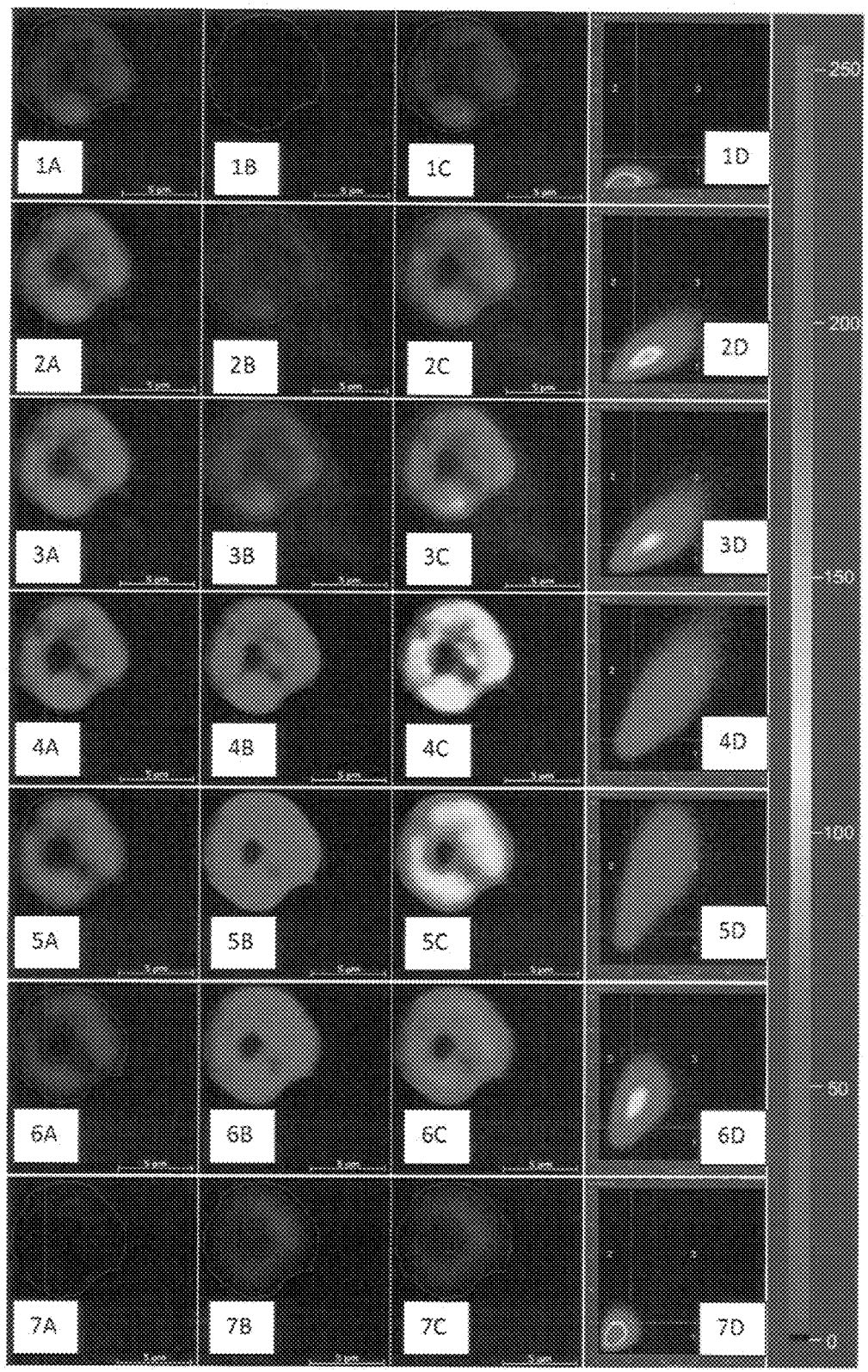
FIG. 6 depicts co-localization analysis of β- and δ-giardin within seven representative optical sections of Giardia lamblia trophozoites (FIGS. 6-1A, B, C, D-FIGS. 6-7A,B,C, D). Optical sectioning was conducted from the ventral side (top panels.

For in-depth analysis of β- and δ-giardin localization within the ventral disc, methanol-fixed trophozoites were double-labeled with antibodies against recombinant β- and δ-giardin, and then subjected to high-resolution scanning along the Z axis. Scanning of the multiple focal planes of entire trophozoites or of ventral disc alone identified specific immunoreactivity for each giardin within the ventral disc. Seven representative optical sections (from 54 acquired) of a trophozoite demonstrate different degree of co-localization of β- and δ-giardin in the ventral disc along the Z axis (FIG. 6). Scatter plots show the quantitative distribution of florescence signal (intensity) between two channels (β-giardin green and δ-giardin red) together with the number of co-localized pixels for each optical section presented. The disc areas, in which β- and δ-giardin are co-localized, are also is shown in the form of yellow pixels in the 2-channel micrographs for every optical section (FIG. 6).

Figure 7:
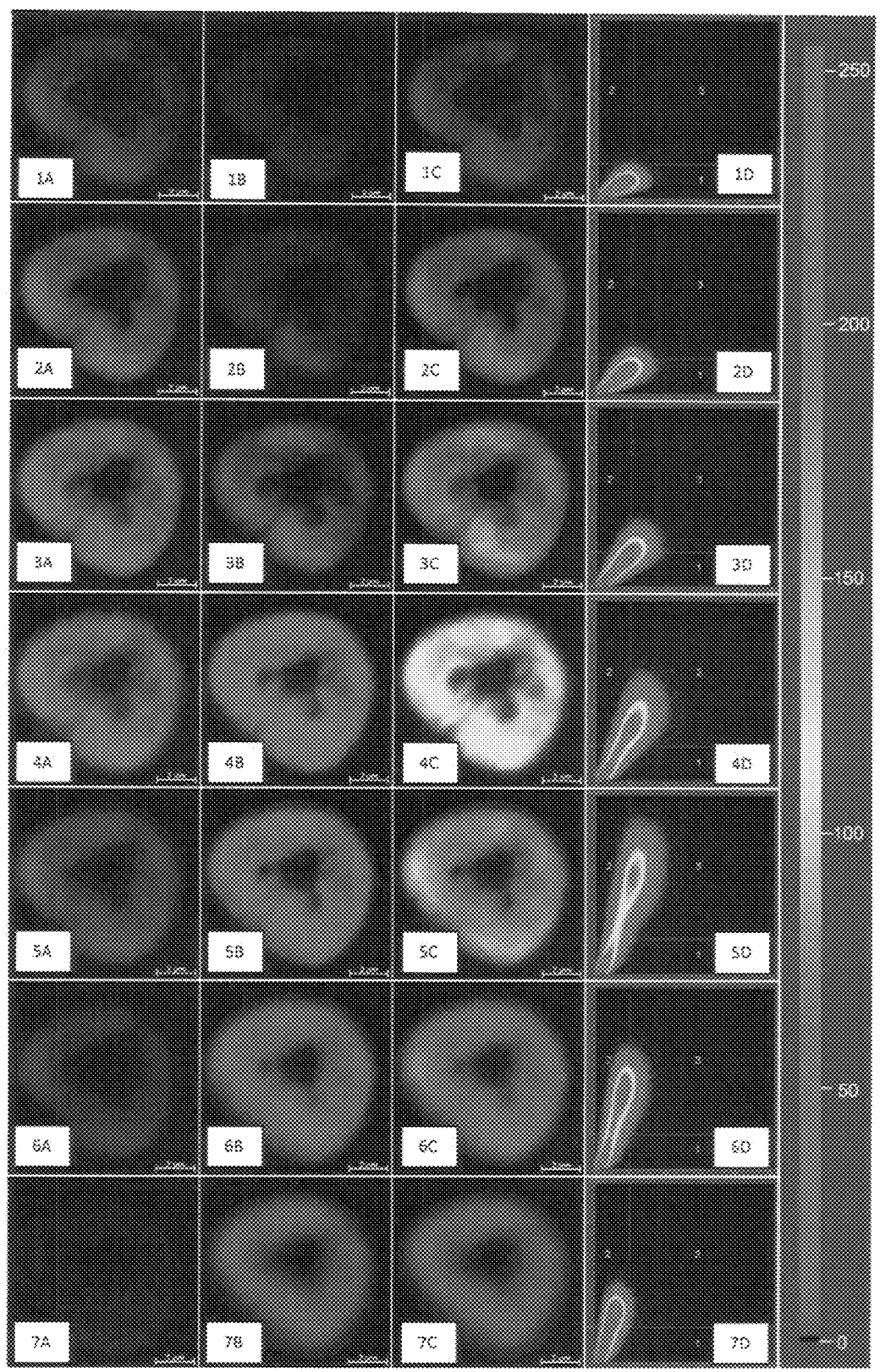

The results of the quantitative co-localization as well as single- and multi-channel confocal images demonstrate the gradual shift in the intensity of immunoreactivity for β- and δ-giardin (FIG. 6). For δ-giardin, a higher intensity was observed between mid-section and the ventral side of the ventral disc. In contrast, higher intensity of immunoreactivity for β-giardin was localized between the mid-section and dorsal side of the ventral disc. The maximum degree of co-localization of β- and δ-giardin was found in mid-section of the ventral disc that can be observed on the 2-channel micrographs as the highest number of yellow pixels, as well as in the scatter plot showing the greatest number of pixels in area #3 (FIG. 6). This pattern of β- and δ-giardin distribution within the ventral disc is also was confirmed by 2 independent quantitative parameters of co-localization: Pearson's Correlation coefficient and Mender's Overlap coefficient (Adler and Parmryd. 2010. *Cytometry* (Part A) 77(8):733-742; Manders et al. 1993. *J. Microscopy* 169:375-382). Both parameters acquired the highest values, 0.65 and 0.91 respectively, in the mid section of the ventral disc (FIG. 6). Quantitative co-localization analysis of the higher resolution images (2048× 2048 pixels), resulting from the optical sectioning of the ventral disc alone, revealed identical pattern for distribution of β- and δ-giardin along the Z axis of the ventral disc, as described above. Seven representative optical sections (from 22 acquired) along with pixel-co-localization graphs, and Pearson's and Mander's coefficient values are shown in FIG. 7. Again, stronger intensity of the Alexa633 (δ-giardin) fluorophore is observed in the top (ventral side of the ventral disc) optical sections. In following lower panels (mid-section of the disc) Alexa633 and FITC have comparable intensities and a greater degree of co-localization, that is also supported by the scatter plots together with Pearson's Correlation and Mander's Overlap coefficients values. 0.33 and 0.81 respectively (FIG. 7). Bottom panels, that represent optical sections from the dorsal side of the ventral disc, illustrate predominantly FITC fluorescence and lower values for quantitative parameters of co-localization.

Figure 8:
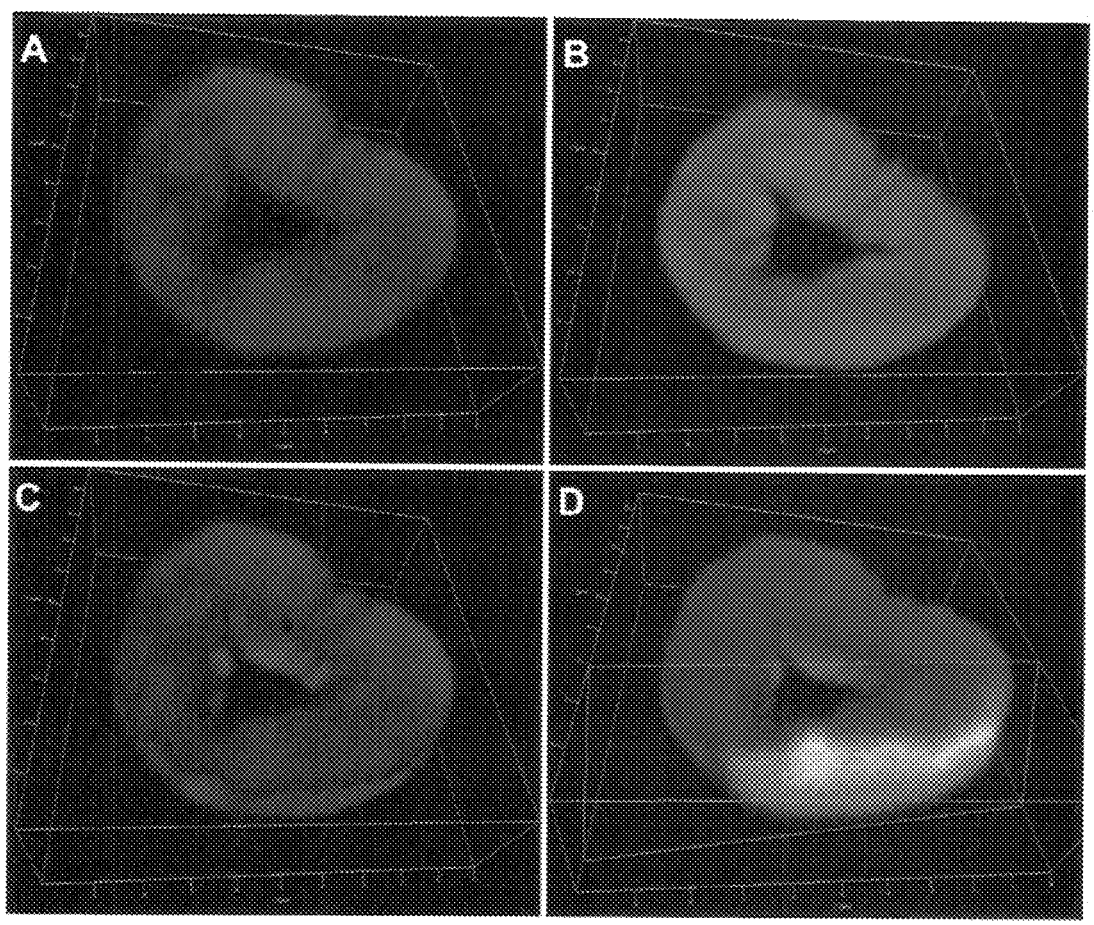
FIGS. 8A-8D depict the three-dimensional projection image of the Giardia lamblia ventral disc, positioned with the ventral side upwards.

A three-dimensional (3D) representation of the spatial localization of β- and δ-giardins to the ventral disc, positioned with the ventral side upwards, was generated using AxioVision 4-D software, (FIG. 8). A 3D distribution of the δ-giardin (red fluorescence) to the ventral disc is shown in panel 8a, and for β-giardin in panel 8b. Spatial localization of both δ- and β-giardin within the ventral disc, revealed δ-giardin on the ventral side and β-giardin on the dorsal side (FIG. 8C). A section through the disc (panel 8d) shows δ- and β-giardin co-localization in the form of yellow pixels. An identical localization of β- and δ-giardins was observed in a dye swap experiment when the trophozoites were labeled with FITC-conjugated mouse anti-goat IgG (Sigma) and Alexa633-conjugated goat anti-rabbit IgG (H+L) (Invitrogen) antibodies (data not shown), demonstrating that distribution of the immunoreactivity for β- and δ-giardins was not affected by the spectral properties of the fluorophores.

In summary, the present immunofluorescence-based localization study is consistent with earlier reports that identified β-giardin associated with the ventral disc (Crossley and Holberto, supra; Holberton and Ward, supra). This study demonstrated for the first time that δ-giardin, even though it shares a great degree of co-localization with β-giardin, is present more ventrally and therefore is closest to the side of the ventral disc that makes contact with host cells. It remains unclear how antibodies to β-giardin and δ-giardin that are known to be associated with the ventral disc can bind PF-fixed *G. lamblia* trophozoites. Whether β-giardin or δ-giardins can bind to host cells in vitro, as has been observed for alpha-1 giardin (Weiland at al. 2005, supra) remains to be determined.

The mouse hybridoma cell lines 2G9-11 and 5E11-19 have been deposited with the American Type Culture Collection (ATCC), 10801 University Blvd., Manassas, Va. 20110-2209 on Aug. 24, 2011, under accession number PTA-12047 and accession number PTA-12048, respectively, as a patent deposit under the Budapest Treaty on the International Recognition of the Deposit of Microorganisms for the Purposes of Patent Procedure. The subject cell lines have been deposited under conditions that assure that access to the cell line will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A hybridoma cell line that produces a monoclonal antibody which specifically and selectively binds one or more epitopes of the *G. lamblia* δ-giardin protein wherein said protein comprises an amino acid sequence shown in SEQ ID NO: 2 and wherein said hybridoma cell line is 5E11-19 deposited with ATCC as Patent Deposit Number PTA-12048.

2. A monoclonal antibody produced by the hybridoma cell line of claim 1.

3. A monoclonal antibody having the binding characteristics of the monoclonal antibody produced by the hybridoma cell line 5E11-19 deposited with ATCC as Patent Deposit Number PTA-12048.

4. The antibody according to claim 2, wherein said antibody is labeled with a detectable moiety.

5. The antibody of claim 4, wherein the detectable moiety is selected from the group consisting of a radioactive label, an enzyme, a specific binding pair component, a colloidal dye substance, a fluorchrome, a reducing substance, a latex, digoxigenin, a metal, a particulate, dansyl lysine, an antibody, protein A, protein G, protein L, an electron dense material, and a chromophore.

6. The antibody according to claim 2 wherein the antibody is attached to a solid or substantially solid substrate.

7. The antibody according to claim 6, wherein the solid or substantially solid substrate includes a component selected from the group consisting of a gel, a hydrogel, a resin, a bead, nitrocellulose, a nylon filter, a microtiter plate, a culture flask, and a polymeric material.

8. A *G. lamblia* diagnostic kit, comprising the monoclonal anti-recombinant δ-giardin-specific antibody of claim 2 and instructions for the use of the kit.

* * * * *

SEQUENCE LISTING

```
<160> NUMBER OF SEQ ID NOS: 9

<210> SEQ ID NO 1
<211> LENGTH: 882
<212> TYPE: DNA
<213> ORGANISM: Giardia lamblia virus

<400> SEQUENCE: 1
atggtcaggg ccaaatgcgc gccttctgcc ctctgtttca taattattaa tagtccgctt      60
ttgcgccaga aaaaaatgac caccgtctcc acgtcgtttt ctctcaagga ccgcctcgca     120
aagatcaaca gccgtgtgac cgactttcac gaggacttca agaggcaggt tgacgagacc     180
aagcaggttg acctcgagag gttcgagctc atccagaacg ggattgagca ccttgacaag     240
atcctccagt tggagaccga gcgagcgacc aagcgcctcg atgacatccg caagaagttc     300
accacccgca taatggacac aagagatgcg ctcggggcct ctgtgagcct ccacacgaag     360
gagaacaatg acaacttctc cgacctcgcc cacaagtgca gacacgccat ggcgaagatc     420
gcccaggagc acgacgatct gctggagtct atccgctact tcaagaccag tgccgaggag     480
tcctttggcg cctttattgg caatctcacc aacgagcgca ataccaggat ggcgctggcg     540
acagagatct acagcaaggt ggaccgcgac ctcaagcatg ccaccgacat gaatgaccgt     600
gcgcgtgcag accgtgagca gagcatcgac gagtacctcc gcgactccga gatcctgagc     660
aggcactatg agtccatcgc acgcgacggt gtcgtctcgc tgtctgcaga gtgcaaggtt     720
ctcgccggcg tcgttgctga gctgattgcg acccgcaaga ccagctacga cgagattgtg     780
aggaccatgg gctctgtcct cgacggtctc cagaacaaca tgaagaagat ctcgaccttc     840
attcgtccag aggacgacca ggaggagaag tttgtcttct aa                         882

<210> SEQ ID NO 2
<211> LENGTH: 293
<212> TYPE: PRT
<213> ORGANISM: Giardia lamblia virus

<400> SEQUENCE: 2
```

```
Met Val Arg Ala Lys Cys Ala Pro Ser Ala Leu Cys Phe Ile Ile Ile
1               5                   10                  15

Asn Ser Pro Leu Leu Arg Gln Lys Lys Met Thr Thr Val Ser Thr Ser
            20                  25                  30

Phe Ser Leu Lys Asp Arg Leu Ala Lys Ile Asn Ser Arg Val Thr Asp
        35                  40                  45

Phe His Glu Asp Phe Lys Arg Gln Val Asp Glu Thr Lys Gln Val Asp
    50                  55                  60

Leu Glu Arg Phe Glu Leu Ile Gln Asn Gly Ile Glu His Leu Asp Lys
65                  70                  75                  80

Ile Leu Gln Leu Glu Thr Glu Arg Ala Thr Lys Arg Leu Asp Asp Ile
                85                  90                  95

Arg Lys Lys Phe Thr Thr Arg Ile Met Asp Thr Arg Asp Ala Leu Gly
            100                 105                 110

Ala Ser Val Ser Leu His Thr Lys Glu Asn Asn Asp Asn Phe Ser Asp
        115                 120                 125

Leu Ala His Lys Cys Arg His Ala Met Ala Lys Ile Ala Gln Glu His
    130                 135                 140

Asp Asp Leu Leu Glu Ser Ile Arg Tyr Phe Lys Thr Ser Ala Glu Glu
145                 150                 155                 160

Ser Phe Gly Ala Phe Ile Gly Asn Leu Thr Asn Glu Arg Asn Thr Arg
                165                 170                 175

Met Ala Leu Ala Thr Glu Ile Tyr Ser Lys Val Asp Arg Asp Leu Lys
            180                 185                 190

His Ala Thr Asp Met Asn Asp Arg Ala Arg Ala Asp Arg Glu Gln Ser
        195                 200                 205

Ile Asp Glu Tyr Leu Arg Asp Ser Glu Ile Leu Ser Arg His Tyr Glu
    210                 215                 220

Ser Ile Ala Arg Asp Gly Val Val Ser Leu Ser Ala Glu Cys Lys Val
225                 230                 235                 240

Leu Ala Gly Val Val Ala Glu Leu Ile Ala Thr Arg Lys Thr Ser Tyr
                245                 250                 255

Asp Glu Ile Val Arg Thr Met Gly Ser Val Leu Asp Gly Leu Gln Asn
            260                 265                 270

Asn Met Lys Lys Ile Ser Thr Phe Ile Arg Pro Glu Asp Asp Gln Glu
        275                 280                 285

Glu Lys Phe Val Phe
    290

<210> SEQ ID NO 3
<211> LENGTH: 780
<212> TYPE: DNA
<213> ORGANISM: Giardia lamblia virus

<400> SEQUENCE: 3
atggacaagc cgacgacct cacccgcagt gcgaccgaga cggcggtcaa gctcagcaac        60
atgaaccagc gcgtcagcag gttccacgac aagatggaga acgagatcga ggtccgccgc       120
gtcgacgacg acacgcgcgt gaagatgatc aaggacgcca tcgcacacct cgacaggctc       180
atccagacgg agtcgaggaa cgccaggcc tcgttcgagg acatccgcga ggaggtcaag        240
aagtccgccg acaacatgta cctaacgatc aaggaggaga tcgacaccat ggctgcaaac       300
ttccgcaagt cccttgcgga gatgggcgac acactcaaca acgttgagac aaatctccag       360
aaccagatcg ccatccataa cgacgccatc gcggctctca ggaaggaggc cctcaagagc       420
```

```
ctgaacgatc tcgagacggg cattgccacg gagaacgcag aaaggaagaa gatgtacgac    480
cagctcaacg agaaggtcgc agagggcttc gcccgcatct ccgccgcgat cgagaaggag    540
acgatcgccc gcgagagggc cgttagcgct gccacgacag aagcgctcac aaacacgaag    600
ctcgtcgaga agtgcgtcaa cgagcagctc gagaacgtcg cctcggagat ccgcgctatc    660
caggaggaga tcgaccgcga aaggccgaa cgcaaggagg cagaggacaa gatcgtcaac    720
actctcgagg acgtcgtctc gaagatccag ggcggcctct cgatggtcac aaagcactaa    780
```

<210> SEQ ID NO 4
<211> LENGTH: 259
<212> TYPE: PRT
<213> ORGANISM: Giardia lamblia virus
<400> SEQUENCE: 4

```
Met Asp Lys Pro Asp Asp Leu Thr Arg Ser Ala Thr Glu Thr Ala Val
1               5                   10                  15

Lys Leu Ser Asn Met Asn Gln Arg Val Ser Arg Phe His Asp Lys Met
            20                  25                  30

Glu Asn Glu Ile Glu Val Arg Arg Val Asp Asp Thr Arg Val Lys
        35                  40                  45

Met Ile Lys Asp Ala Ile Ala His Leu Asp Arg Leu Ile Gln Thr Glu
50                  55                  60

Ser Arg Lys Arg Gln Ala Ser Phe Glu Asp Ile Arg Glu Glu Val Lys
65                  70                  75                  80

Lys Ser Ala Asp Asn Met Tyr Leu Thr Ile Lys Glu Glu Ile Asp Thr
                85                  90                  95

Met Ala Ala Asn Phe Arg Lys Ser Leu Ala Glu Met Gly Asp Thr Leu
            100                 105                 110

Asn Asn Val Glu Thr Asn Leu Gln Asn Gln Ile Ala Ile His Asn Asp
        115                 120                 125

Ala Ile Ala Ala Leu Arg Lys Glu Ala Leu Lys Ser Leu Asn Asp Leu
    130                 135                 140

Glu Thr Gly Ile Ala Thr Glu Asn Ala Glu Arg Lys Lys Met Tyr Asp
145                 150                 155                 160

Gln Leu Asn Glu Lys Val Ala Glu Gly Phe Ala Arg Ile Ser Ala Ala
                165                 170                 175

Ile Glu Lys Glu Thr Ile Ala Arg Glu Arg Ala Val Ser Ala Ala Thr
            180                 185                 190

Thr Glu Ala Leu Thr Asn Thr Lys Leu Val Glu Lys Cys Val Asn Glu
        195                 200                 205

Gln Leu Glu Asn Val Ala Ser Glu Ile Arg Ala Ile Gln Glu Glu Ile
    210                 215                 220

Asp Arg Glu Lys Ala Glu Arg Lys Glu Ala Asp Lys Ile Val Asn
225                 230                 235                 240

Thr Leu Glu Asp Val Val Ser Lys Ile Gln Gly Gly Leu Ser Met Val
                245                 250                 255

Thr Lys His
```

<210> SEQ ID NO 5
<211> LENGTH: 28
<212> TYPE: DNA
<213> ORGANISM: Artificial Sequence
<220> FEATURE:
<223> OTHER INFORMATION: Chemically Synthesized
<400> SEQUENCE: 5

```
aatttggtac catggacaag cccgacga                                              28

<210> SEQ ID NO 6
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 6
gggttcgaat tagtgctttg tacc                                                  24

<210> SEQ ID NO 7
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 7
ctgtacgacg atgacgataa g                                                     21

<210> SEQ ID NO 8
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 8
tcatccgcca aaacagccaa g                                                     21

<210> SEQ ID NO 9
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 9
cgattaaata aggagg                                                           16
```